United States Patent
Blasdell et al.

[11] Patent Number: 6,135,109
[45] Date of Patent: Oct. 24, 2000

[54] INHALATION APPARATUS

[76] Inventors: Richard J. Blasdell, 13231 N. 14th Pl., Phoenix, Ariz. 85022; Raymond L. Blasdell, 691 E. Fairway Dr., Litchfield Park, Ariz. 85340

[21] Appl. No.: 09/134,701

[22] Filed: Aug. 14, 1998

Related U.S. Application Data

[60] Provisional application No. 60/055,885, Aug. 15, 1997.
[51] Int. Cl.[7] .................................................. A61M 16/06
[52] U.S. Cl. .................................. 128/206.28; 128/206.21
[58] Field of Search .......................... 128/206.21, 206.28, 128/207.12, 203.29, 205.25

[56]  References Cited

U.S. PATENT DOCUMENTS

| | | | |
|---|---|---|---|
| 4,015,598 | 4/1977 | Brown | 128/188 |
| 4,794,921 | 1/1989 | Lindkvist | 128/207.13 |
| 4,807,617 | 2/1989 | Nesti | 128/203.29 |
| 5,018,519 | 5/1991 | Brown . | |
| 5,355,878 | 10/1994 | Griffiths et al. | 128/205.25 |
| 5,676,133 | 10/1997 | Hickle et al. | 128/205.25 |
| 5,937,851 | 8/1999 | Serowski et al. | 128/202.27 |

*Primary Examiner*—John G. Weiss
*Attorney, Agent, or Firm*—Parsons & Goltry; Robert A. Parsons; Michael W. Goltry

[57]  ABSTRACT

An inhalation mask assembly for administering a respirable gas to an individual, which individual includes a facial area having a respiratory organ for receiving respirable gas and for expelling exhaust gas, the exhaust gas having a moisture content, the inhalation mask assembly comprising a generally cup-shaped first body receivable against the facial area for substantially enclosing the respiratory organ, an inhalation assembly for communicating respirable gas to the first body, an exhalation valve assembly for conducting exhaust gas from the first body, a generally cup-shaped second body carried by the first body for receiving exhaust gas from the exhalation valve assembly, a substantially transparent region carried by the second body, the substantially transparent region having a surface adjacent the exhalation valve assembly for accumulating moisture from the exhaust gas, and an exhalation assembly for conducting exhaust gas from the second body.

12 Claims, 9 Drawing Sheets

INHALATION APPARATUS

This application claims the benefit of U.S. Provisional Application 60/055,885, filed Aug. 15, 1997.

FIELD OF THE INVENTION

This invention relates generally to the field of inhalation apparatus and, more particularly, to improvements in inhalation masks for use in an inhalation system.

BACKGROUND OF THE INVENTION

Inhalation or respiratory systems for administering respirable gas to an individual are well known. Especially recognized are apparatus employed in the medical and dental arts for dispensing anesthetic and analgesic gases to a patient. Exemplary familiar gases are oxygen and nitrous oxide.

Typically, inhalation systems include a source of a selected pressurized gas and means to deliver the gas to the external respiratory organs of the patient. A breathing device, such as a mask, is fitted to the face of the patient to embrace the nose and/or the mouth. The source, which may be either portable or fixed, usually includes a flow regulator. A delivery conduit, generally in the form of a flexible hose, communicates between the source and the breathing device. Optionally, the system may include scavenging apparatus comprising a return conduit extending from the breathing device to a source of vacuum.

The prior art has devised an array of personal breathing devices in numerous structural configurations. More commonly referred to as inhalation masks or facemasks, the devices serve a variety of specific functions. Known, for example, are masks that extend over the mouth and the nose of the patient while others receive only the nose. Commonly, masks include a fitting for attachment of a gas delivery conduit. Infrequently, an exhalation valve is incorporated into a mask to prevent the entrance of ambient air.

Recently, there has arisen a concern over expired gas. A solution proposed by the prior art is in the form of a scavenger valve attachment for retrofit to certain pre-existing inhalation masks. To accommodate the attachment, the mask must include an exhalation valve body of exacting configuration that must be removed. In addition to the wastefulness of the discarded valve body and the inconvenience of effecting the conversion, the attachment is exceedingly complex having an encumbered chamber and valving assembly.

Other inadequacies of the prior art are equally disconcerting. Masks with metallic components, for example, are not compatible with the use of X-ray equipment. Ever present is the concern over proper fit and sealing engagement with the facial area while concurrently ensuring patient comfort. Prior art inhalation masks also prevent medical personnel from easily determining whether the patient wearing the mask is breathing.

It would be highly advantageous, therefore, to remedy the foregoing and other deficiencies inherent in the prior art.

It is a purpose of the present invention to provide a new and improved inhalation mask assembly.

It is another purpose of the present invention to provide a new and improved inhalation mask assembly especially adapted for use in combination with conventional medical and dental inhalation systems.

It is still another purpose of the present invention to provide a new and improved inhalation mask assembly having ameliorated means for sealing a mask to the facial area of a user.

It is a further purpose of the present invention to provide a new and improved inhalation mask assembly including a mask that readily conforms to the face of the user and is exceedingly comfortable to wear.

It is still a further purpose of the present invention to provide a new and improved inhalation mask assembly that is compatible with X-ray technology.

It is yet still a further purpose of the present invention to provide a new and improved inhalation mask assembly that may be fabricated in various configurations to accommodate selected applications.

It is another purpose of the present invention to provide a new and improved inhalation mask assembly having a scavenger for conducting exhaust gas away from the user wearing the inhalation mask assembly.

It is still another purpose of the present invention to provide a new and improved inhalation mask assembly that allows a medical practitioner to monitor the breathing of a user wearing the inhalation mask assembly without the need for additional monitoring equipment.

SUMMARY OF THE INVENTION

The above problems and others are at least partially solved and the above purposes and others are realized in a new and improved inhalation mask assembly for administering a respirable gas to an individual, which individual includes a facial area having a respiratory organ for receiving respirable gas and for expelling exhaust gas, the exhaust gas having a moisture content when expelled from the respiratory organ. In a specific embodiment, the inhalation mask assembly of the present invention is generally comprised of a generally cup-shaped first body receivable against the facial area for substantially enclosing the respiratory organ, an inhalation assembly for communicating respirable gas to the first body and an exhalation valve assembly for conducting exhaust gas from the first body. Further included is a generally cup-shaped second body carried by the first body for receiving exhaust gas from the exhalation valve assembly. The second body includes a substantially transparent or portion or region having a surface adjacent the exhalation valve assembly for accumulating moisture from the exhaust gas. An exhalation assembly conducts exhaust gas from the second body.

BRIEF DESCRIPTION OF THE DRAWINGS

The foregoing and further and more specific objects and advantages of the instant invention will become readily apparent to those skilled in the art from the following detailed description thereof taken in conjunction with the drawings in which.

DETAILED DESCRIPTION OF A PREFERRED EMBODIMENT

The present invention provides, among other things, a new and improved inhalation mask assembly for administering or otherwise conducting a respirable gas to an individual, which individual includes a facial area having a respiratory organ for conducting respirable gas into the individual's respiratory tract and for expelling exhaust gas from the individual's respiratory tract, the exhaust gas having a moisture content or level when expelled from the respiratory organ in accordance with normal exhaust gas expelled from human beings.

Figure 1:
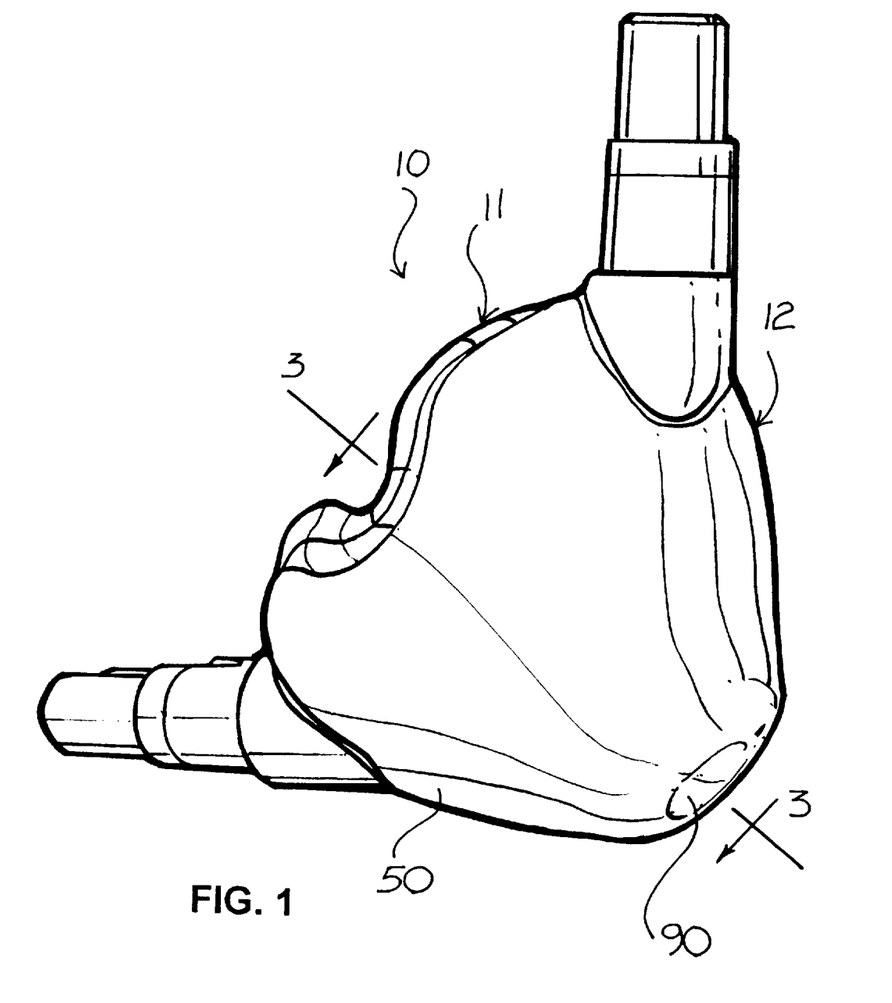
FIG. 1 illustrates an inhalation mask assembly, in accordance with a preferred embodiment of the present invention.

Turning now to the drawings, in which like reference characters indicate corresponding elements throughout the several views, attention is first directed to FIG. 1 which illustrates an inhalation mask assembly generally designated by the reference character 10, in accordance with a preferred embodiment of the present invention. Inhalation mask assembly 10 includes a mask 11 and a scavenger 12 carried by or otherwise engaged with mask 11.

Figure 2:
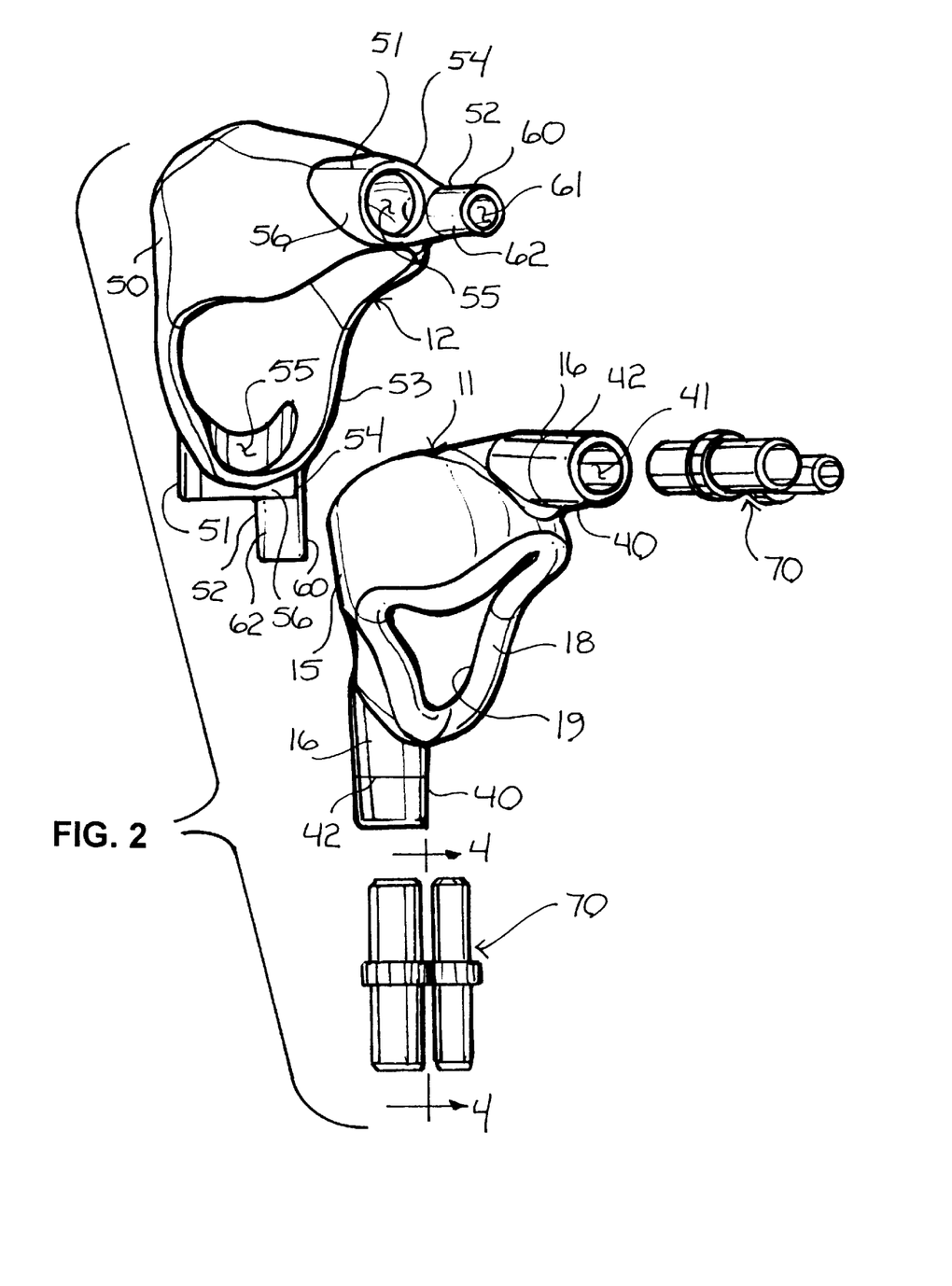
FIG. 2 illustrates an exploded view of the inhalation mast assembly of FIG. 1.
Figure 3:
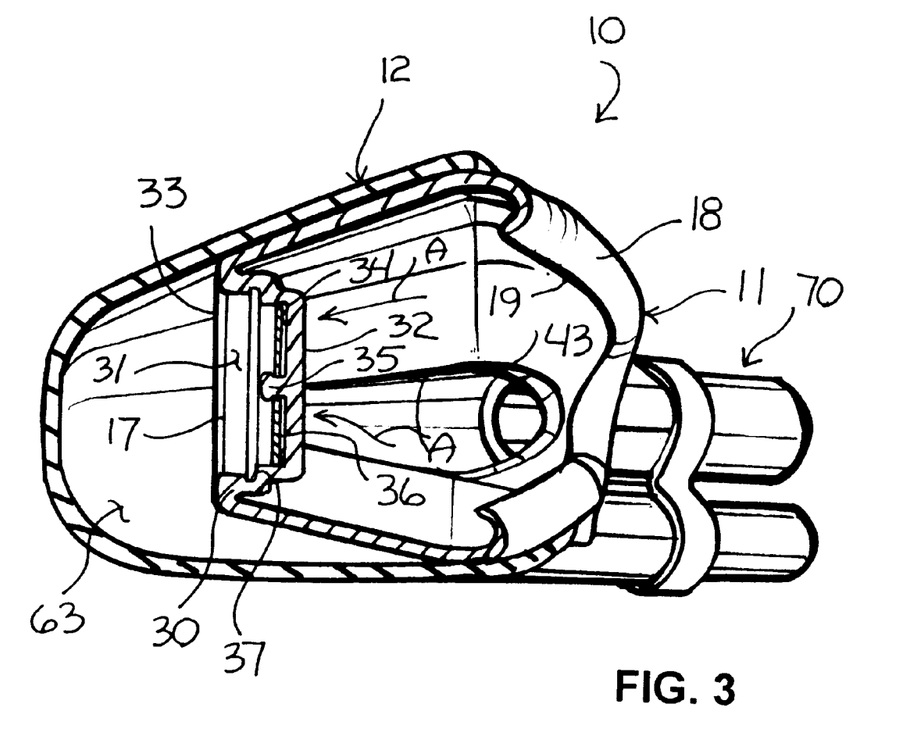
FIG. 3 illustrates a sectional view taken along line 3—3 of FIG. 1.

With attention directed to FIG. 2 illustrating an exploded view of inhalation mask assembly 10 of FIG. 1, mask 11 includes a body 15 having an inhalation assembly 16 and exhalation valve assembly 17 shown best in FIG. 3 showing a sectional view taken along line 3—3 of FIG. 2. Preferably, two inhalation assemblies 16 are included, one extending from either lateral side of body 15. The single exhalation valve assembly 17 is shown located at a frontal midpoint. Body 15 is generally cup-shaped and terminates with a rearwardly directed peripheral edge 18. As shown in FIG. 3, edge 18 comprises a terminal portion of body 15 and is inturned to form a semi-cylindrical bead having an inwardly directed free edge 19. Body 15 is sized to receive at least one of the external respiratory organs, such as the nose, of an individual. Edge 18 is contoured to be received against the facial area surrounding the nose.

Body 15 is preferably molded of a flexible elastic material such as the thermoplastic elastomer found under the exemplary trademark KRATON®. Being of reduced thickness, the terminal portion forming edge 18 is readily deformable to be pliantly received against the facial area in sealing engagement therewith.

In accordance with the immediately preferred embodiment of the present invention, exhalation valve 17 includes integrally formed exhalation valve body 30 projecting inwardly into body 15. Body 30 defines a bore 31 extending therethrough functioning as an outlet port which includes an inlet end 32 and an outlet end 33. Outwardly directed annular valve seat 34 is formed in bore 31 proximate inlet end 32. Post 35 is coaxially held within bore 31 by a spider-like arrangement of support members that extend radially between post 35 and the sidewalls of bore 31 intermediate valve seat 34 and inlet end 32. Valve disc 36, preferably a relatively thin resiliently deformable member that may also be fabricated of a thermoplastic material, is carried by post 35. Annular groove 37, functioning as an attachment receiving means, is formed coaxially into bore 31 proximate outlet end 33.

Valve disc 36 resides against valve seat 34 in the closed position as seen in FIG. 3. In response to inhalation of the individual, valve disc 36 is drawn with greater force into sealing engagement with valve seat 34. In response to exhalation of the individual, valve disc 36 deflects from valve seat 34 for exhaust of expired gases in the direction of arrowed lines A. Accordingly, it is seen that disc 36 and valve seat 34 function as an outlet check valve for unidirectional flow of expired gas through bore 31.

With attention directed back to FIG. 2, each inhalation assembly 16 includes an inhalation body 40 projecting from body 15 and having a bore 41 extending therethrough defined by cylindrical sidewall 42. Inhalation body 40 projects angularly rearward from body 15. Accordingly, the outlet end 43 (shown only in FIG. 3) of bore 41 is generally elliptical, being askew to the longitudinal axis of bore 41.

With continuing reference to FIG. 2, supportable by mask 11 is scavenger 12. Scavenger 12 includes a body 50 having inhalation assembly 51 and exhalation assembly 52. Preferably, two inhalation assemblies 51 are included, one extending from either lateral side of body 50. Two exhalation assemblies 52 are also included, one extending from either lateral side of body 50 adjacent one of the respective inhalation valve assemblies 51. Like body 15 of mask 11, body 50 is generally cup-shaped and terminates with a rearwardly directed peripheral edge 53. Body 50 is preferably molded of a flexible elastic material such as the thermoplastic elastomer found under the exemplary trademark KRATON®.

With attention directed back to FIG. 2, each inhalation assembly 51 includes an inhalation body 54 projecting from body 50 and having a bore 55 therethrough defined by cylindrical sidewall 56. Inhalation body 54 projects angularly rearward from body 50. Furthermore, each exhalation assembly 51 includes an exhalation body 60 projecting from body 50 and having a bore 61 therethrough defined by cylindrical sidewall 62. Exhalation body 60 projects angularly rearward from body 50.

Scavenger 12 is carried by mask 11 in spaced relation. As shown in FIG. 2, exhaust valve assembly 17 of mask 11 confronts the frontal portion of body 50 of scavenger 12 to define a space forming an exhaust passage 63 as can be seen with reference to FIG. 3. Furthermore, each inhalation assembly 16 extends into and through a respective inhalation assembly 51 of scavenger 12 extending rearwardly of body 50 of scavenger 12.

Figure 4:
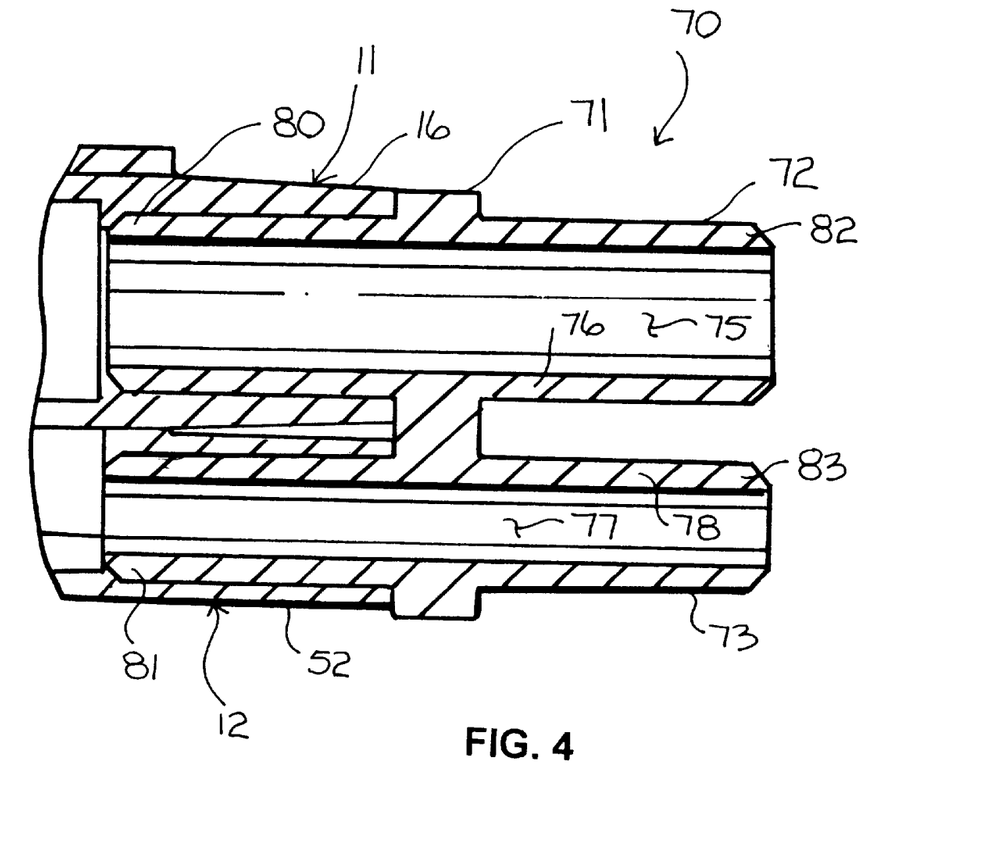
FIG. 4 illustrates a sectional view of a connector taken along line 4—4 of FIG. 2.

A connector assembly 70 is also provided operative for admitting respirable gas into inhalation mask assembly 10 and for conducting exhaust gas from the inhalation mask assembly 10. Preferably two connector assemblies 70 are provided. With attention directed to FIG. 4 illustrating a sectional view taken along line 4—4 of FIG. 2 of one of the connector assemblies 70, connector assembly 70 includes a body 71 having an inlet assembly 72 and an outlet assembly 73 disposed in spaced-apart and substantially parallel and coextensive relation. Inlet assembly 72 includes a bore 75 extending therethrough defined by cylindrical sidewall 76. Furthermore, outlet assembly 73 includes a bore 77 extending therethrough defined by cylindrical sidewall 78.

Inner end 80 of each inlet assembly 72 of connector assembly 70 is matingly and substantially sealingly engagable within a respective inhalation assembly 16 of mask 11, and inner end 81 of each outlet assembly 73 is correspondingly matingly and substantially sealingly engagable within a respective exhalation assembly 52 of scavenger 12. Outer ends 82 and 83 of inlet assembly 72 and outlet assembly 73, respectively, of connector assembly 70 may be coupled to a respirable gas source and a vacuum scavenger apparatus, respectively. In this regard, inlet assembly 72 operates to conduct respirable gas into mask 11 for inhalation by a user. Upon exhalation by the user, exhalation valve assembly 17 will conduct exhaled gas from mask 11 and into exhaust passage 63. Once in the exhaust passage 63, the vacuum scavenger source will pull the exhaled gas outwardly through the outlet assembly 73 of each connector assembly 70. Consistent with the teachings of the present invention, a suitable system operative for supplying a respirable gas to inhalation mask assembly and for providing a vacuum scavenger apparatus for collecting exhaust from the inhalation mask assembly is fully disclosed in U.S. Pat. No. 5,311,862, of which is owned by the present Applicant and incorporated herein by reference.

With attention directed back to FIG. 1, the frontal midpoint of body 50 of scavenger 12 defines a region 90 preferably constructed of a substantially clear or transparent material, such as thermoplastic material, plastic, etc., operative for allowing an observer to look into exhaust passage 63. As a result, during use of inhalation mask assembly 10, the moisture content contained in the exhaust gas exhaled by the user will condense upon the inner surface of region 90. A doctor or observer may look through region 90 and observe whether the user of the inhalation mask assembly 10 is breathing properly by virtue of noticing whether condensation is forming on region 90 of scavenger 12.

Mask 11 may be detachably engagable to scavenger 12. In this regard, mask 11 may be disposable. However, scavenger 12 and connector assembly 70 are preferably constructed to be reusable after suitable cleaning between uses such as by autoclaving. Furthermore, mask 11 and or scavenger 12 may be constructed of a thermoplastic material having a selected and desired scent and a color corresponding to the selected scent as disclosed in U.S. Pat. No. 5,109,839 owned by Applicant and incorporated herein by reference.

Figure 5:
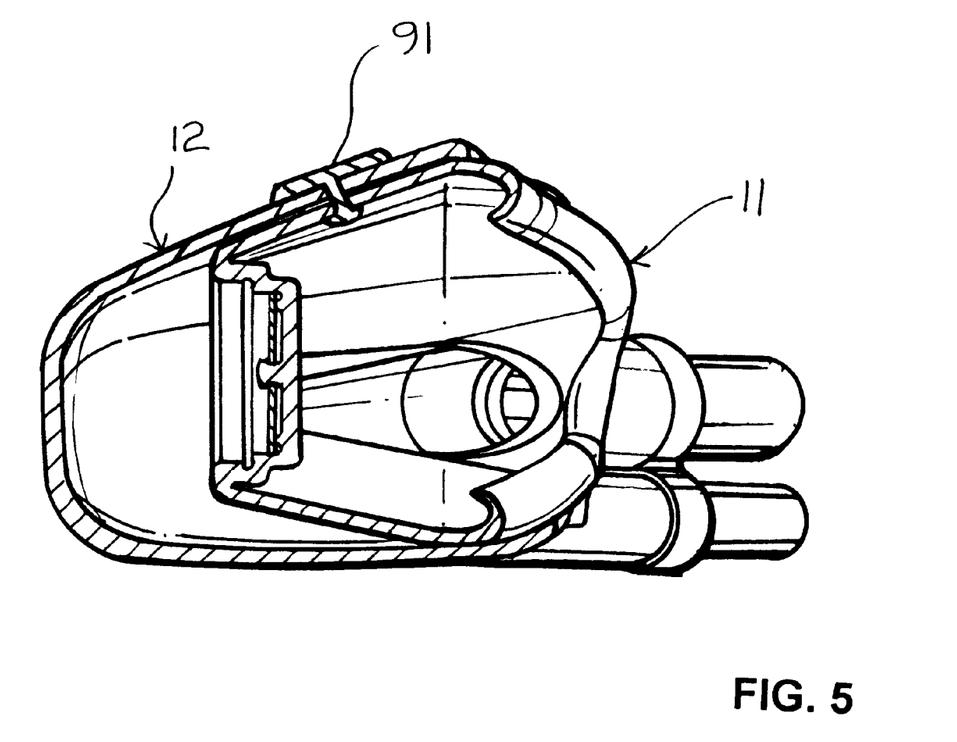
FIG. 5 illustrates a view very similar to the view of FIG. 3.

Although mask 11 may be detachably engagable with scavenger 12, it may be either integrally formed with scavenger 12 or fixedly engaged to scavenger by virtue of a suitable fastener such as rivet 91 shown in FIG. 5.

Figure 6:
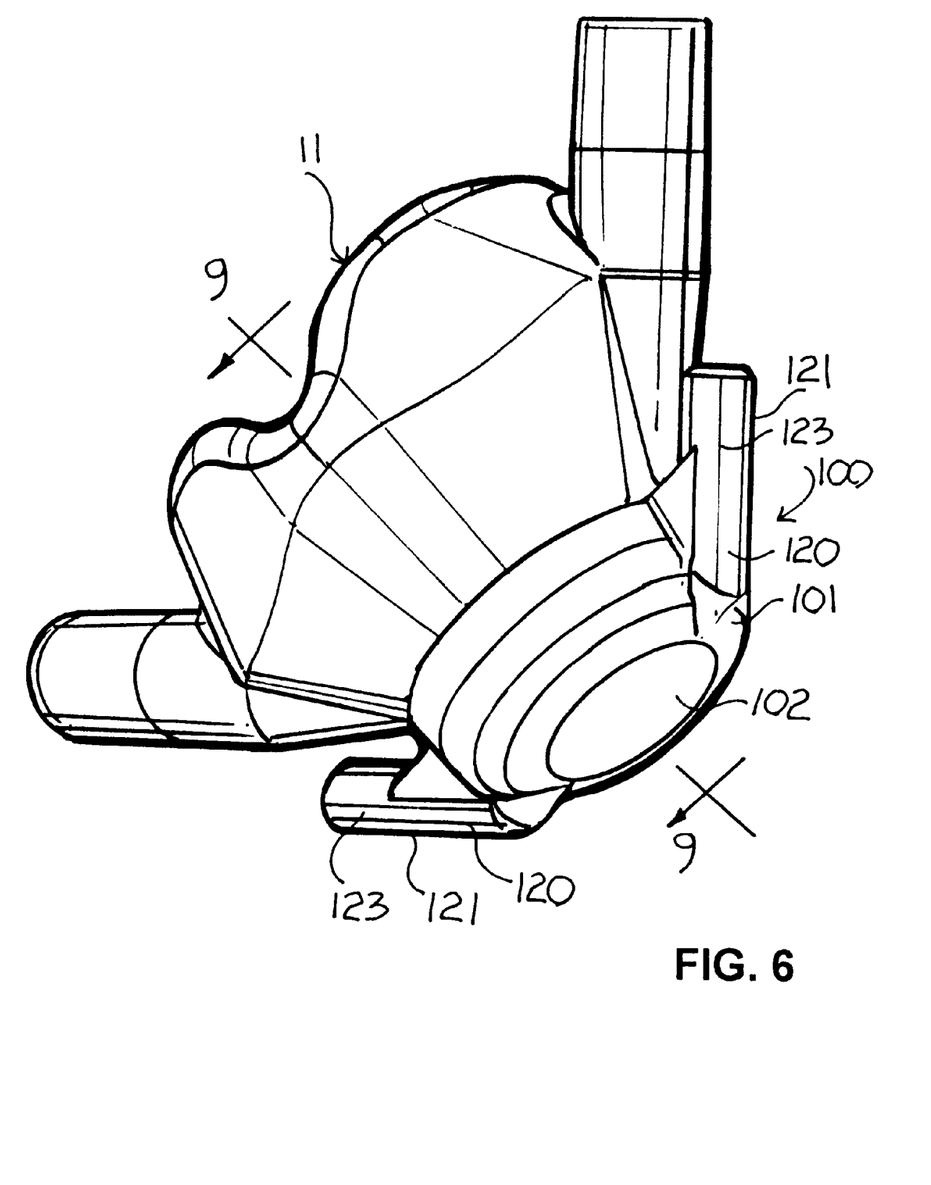
FIG. 6 illustrates an alternate embodiment of an inhalation mask assembly.

With attention directed to FIG. 6, mask 11 is shown coupled to an alternate embodiment of a scavenger generally designated by the reference character 100. Scavenger 100 includes a hollow cup-shaped body 101 closed at the outboard end by an endwall 102 to form a chamber 103 therein (shown in FIG. 8 and FIG. 9). Regarding FIG. 9, scavenger 100 may be coupled to mask 11 by virtue of connector 105. Connector 105, best shown in FIG. 7 and FIG. 8, includes a bore 106 defined by a cylindrical body 107 and opposed annular fingers 108 located at a distal end 109 of body 107 and an outwardly extending annular flange 110 located at a proximal end 111 of body 107. As seen in FIG. 9, annular flange 110 is detachably receivable within annular groove 37 of mask 11 and fingers 108 are correspondingly snappingly and detachably engagable within a pair of opposed arcuate grooves 112 extending inwardly toward chamber 103 from endwall 102. In this manner of construction, a user may easily and detachably engage mask 11 to scavenger 100 and then after use, dispose of mask 11 and clean connector 105 and scavenger 100 by virtue of autoclaving or other suitable cleaning technique prior to reuse.

Figure 7:
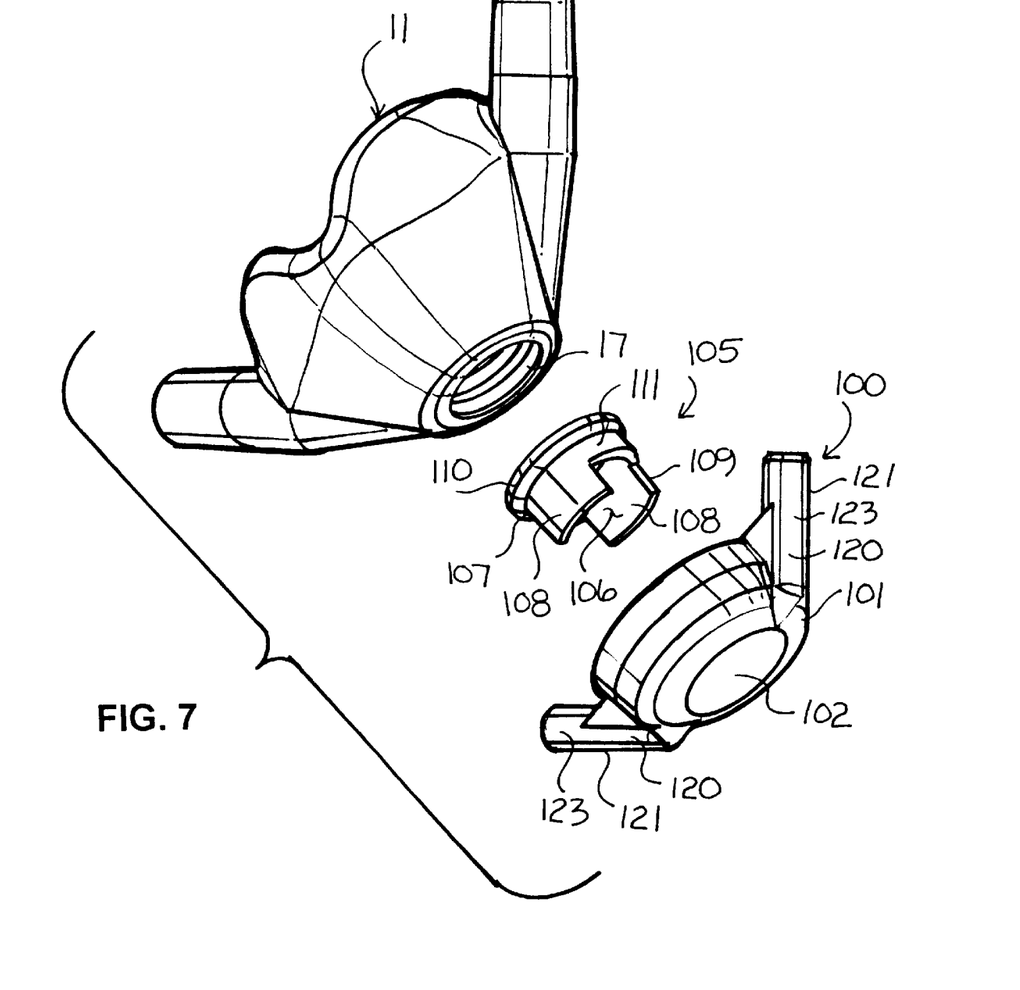
FIG. 7 illustrates an exploded perspective view of the inhalation mask assembly of FIG. 6.
Figure 8:
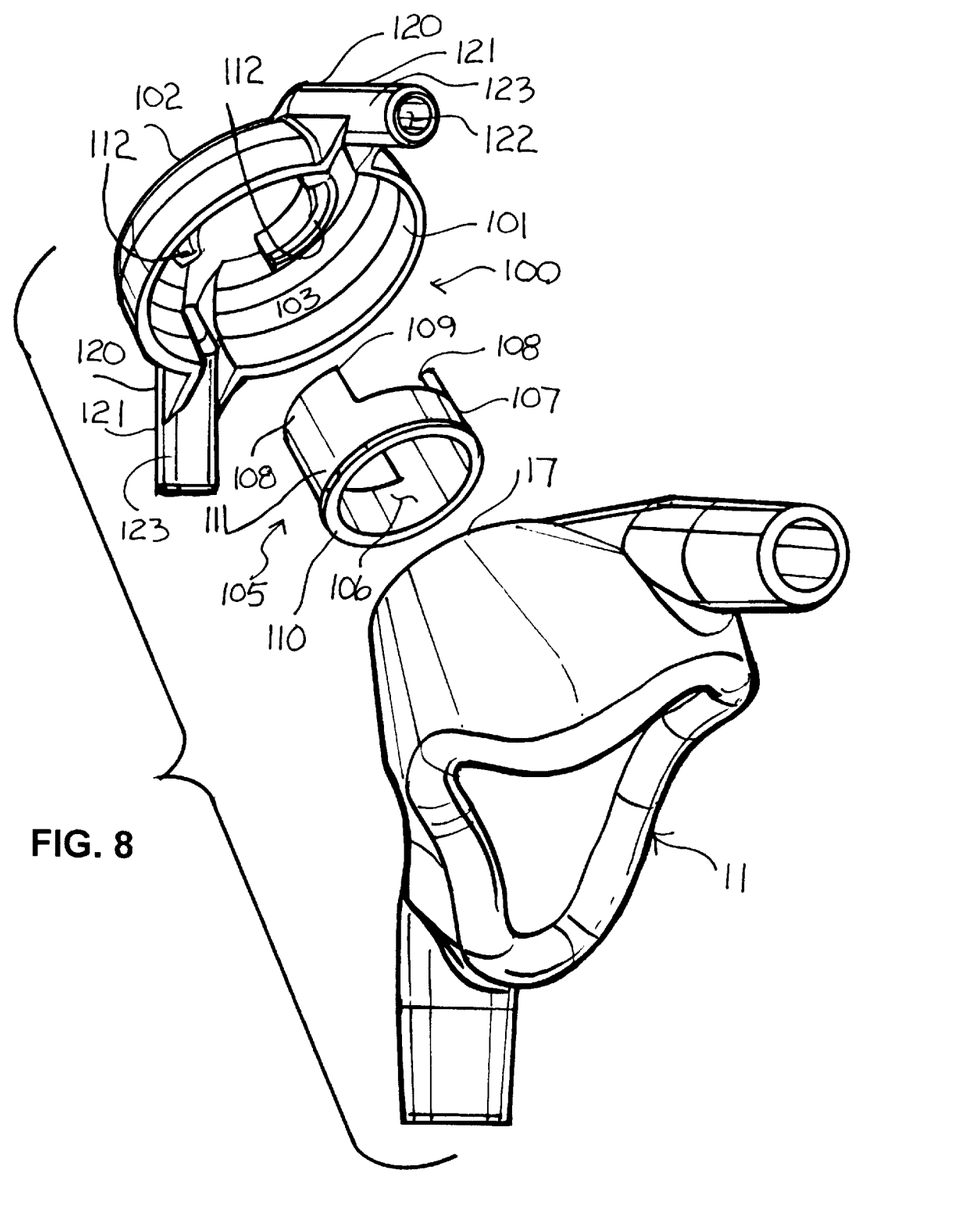
FIG. 8 illustrates another exploded perspective view of the inhalation mask assembly of FIG. 6.
Figure 9:
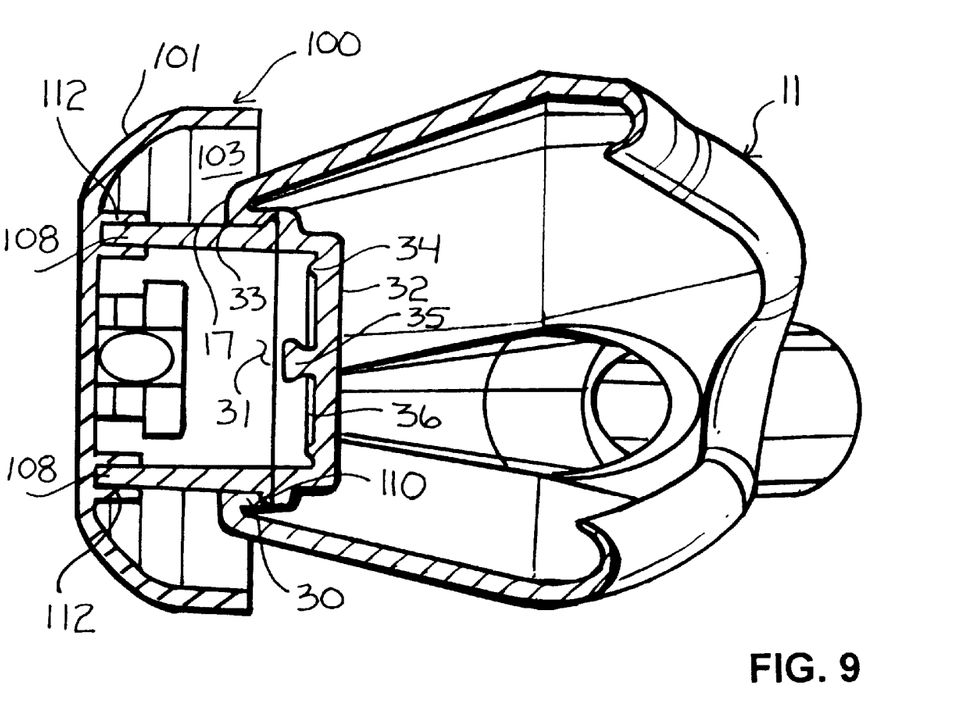
FIG. 9 illustrates a sectional view taken along line 9—9 of FIG. 6.

As seen in FIG. 6, FIG. 7 and FIG. 8, scavenger 100 further includes an exhalation assembly 120. Preferably, two exhalation assemblies 120 are included, one extending from either lateral side of body 101. Each exhalation assembly 120 includes an exhalation body 121 projecting from body 101 and having a bore 122 (shown only in FIG. 8) therethrough defined by cylindrical sidewall 123. Exhalation body 121 projects angularly rearward from body 101. Like the previous embodiment, each exhalation assembly 120 may be coupled to a vacuum scavenger source.

Regarding the preferred teachings, body 101 of scavenger 100 is preferably constructed of a substantially clear substance such as clear plastic or other material so that as a user uses mask 11 and scavenger 100, the user's breath will condense upon endwall 102 of body 101 for allowing an observer, such as a doctor or nurse, to observe the condensation form on endwall 102 as the user breaths. In this way, the observer may monitor the breathing of the user to insure the user is breathing properly and to insure the correct rates and levels of respirable gas are being introduced into mask 11 and that the proper level of vacuum is being maintained from the vacuum scavenger source.

The present invention has been described above with reference to a preferred embodiment. However, those skilled in the art will recognize that changes and modifications may be made in the described embodiments without departing from the nature and scope of the present invention. Various changes and modifications to the embodiment herein chosen for purposes of illustration will readily occur to those skilled in the art. To the extent that such modifications and variations do not depart from the spirit of the invention, they are intended to be included within the scope thereof.

Having fully described the invention in such clear and concise terms as to enable those skilled in the art to understand and practice the same, the invention claimed is:

1. An inhalation mask assembly for administering a respirable gas to an individual, which individual includes a facial area having a respiratory organ for receiving respirable gas and for expelling exhaust gas, the exhaust gas having a moisture content, the inhalation mask assembly comprising:

a generally cup-shaped first body receivable against the facial area for substantially enclosing the respiratory organ and having a frontal midpoint for directly opposing the respiratory organ;

means for communicating respirable gas to the first body;

an exhalation valve assembly carried at the frontal midpoint of the first body for conducting exhaust gas from the first body;

a generally cup-shaped second body carried by the first body for receiving exhaust gas from the exhalation valve assembly;

a substantially transparent region carried by a frontal midpoint of the second body, the substantially transparent region having a surface adjacent to and directly opposing the exhalation valve assembly for accumulating moisture from the exhaust gas; and means for conducting exhaust gas from the second body.

2. The inhalation mask assembly of claim 1, wherein the second body is fixed to the first body.

3. The inhalation mask assembly of claim 1, wherein the second body is removably carried by the first body.

4. The inhalation mask assembly of claim 1, wherein the means for conducting exhaust gas from the first body comprises:

an exhalation valve body carried by the first body and having an inlet end, an outlet end and a bore extending therethrough from the inlet end to the outlet end;

an outlet check valve carried by the exhalation valve body adjacent the inlet end for unidirectional flow of gas through the bore of the exhalation valve body.

5. An inhalation mask assembly for administering a respirable gas to an individual, which individual includes a facial area having a respiratory organ for receiving respirable gas and for expelling exhaust gas, the exhaust gas having a moisture content, the inhalation mask assembly comprising:

a generally cup-shaped first body receivable against the facial area for substantially enclosing the respiratory organ and having a frontal midpoint for directly opposing the respiratory organ;

means for communicating respirable gas to the first body;

an exhalation valve assembly carried at the frontal midpoint of the first body for conducting exhaust gas from the first body;

a substantially transparent region carried by a frontal midpoint of a generally cup-shaped second body, the substantially transparent region having a surface adjacent to and directly opposing the exhalation valve assembly for accumulating moisture from the exhaust gas;

a connector including a body having a proximal end, a distal end and a bore extending therethrough from the proximal end to the distal end;

means for engaging the proximal end with the first body in communication with the exhalation valve assembly;

means for engaging the distal end with the second body, the second body for receiving exhaust gas conducted through the bore of the connector from the exhalation valve assembly, portions of the second body for accumulating moisture from the exhaust gas; and     means for conducting exhaust gas from the second body.

6. The inhalation mask assembly of claim 5, wherein the means for engaging the proximal end with the first body in communication with the exhalation valve assembly comprises:

an engagement element carried by the proximal end; and a detachably engagable complemental engagement element carried by the first body.

7. The inhalation mask assembly of claim 6, wherein the engagement element includes an annular flange.

8. The inhalation mask assembly of claim 7, wherein the complemental engagement element includes an annular groove.

9. The inhalation mask assembly of claim 5, wherein the means for engaging the distal end with the second body comprises:

an engagement element carried by the distal end; and a detachably engagable complemental engagement element carried by the second body.

10. The inhalation mask assembly of claim 9, wherein the engagement element includes opposed annular fingers.

11. The inhalation mask assembly of claim 10, wherein the complemental engagement element includes opposed annular grooves each for detachably receiving one of the opposed annular fingers.

12. The inhalation mask assembly of claim 5, wherein the exhalation valve assembly for conducting exhaust gas from the first cup-shaped body comprises:

an exhalation valve body carried by the first body and having an inlet end, an outlet end and a bore extending therethrough from the inlet end to the outlet end;

an outlet check valve carried by the exhalation valve body adjacent the inlet end for unidirectional flow of gas through the bore of the exhalation valve body.

\* \* \* \* \*